United States Patent [19]

Wallschlaeger

[11] Patent Number: 5,396,913
[45] Date of Patent: Mar. 14, 1995

[54] COSMETIC APPLICATOR

[76] Inventor: Gunnar J. Wallschlaeger, 3998 NW. 4th Ave., Boca Raton, Fla. 33431

[21] Appl. No.: 95,527

[22] Filed: Jul. 26, 1993

[51] Int. Cl.6 .............................................. A45D 40/26
[52] U.S. Cl. ...................................... 132/320; 206/823
[58] Field of Search ............... 132/286, 293, 294, 312, 132/314, 317, 320; 206/581, 823

[56] References Cited

U.S. PATENT DOCUMENTS

| | | | |
|---|---|---|---|
| 3,568,684 | 3/1971 | Reece | 132/1 |
| 3,861,946 | 1/1975 | Waitkins et al. | 428/404 |
| 4,611,611 | 9/1986 | Beal, Jr. | 132/88.7 |
| 4,751,934 | 6/1988 | Moir et al. | 132/79 |
| 4,995,408 | 2/1991 | Wallschlaeger | 132/320 |
| 5,020,553 | 6/1991 | De La Rocha | 132/320 |
| 5,031,647 | 7/1991 | Seidler | 132/317 |
| 5,069,232 | 12/1991 | Staar | 132/320 |

Primary Examiner—Gene Mancene
Assistant Examiner—Frank A. LaViola
Attorney, Agent, or Firm—Eugene Lieberstein

[57] ABSTRACT

A cosmetic applicator comprising a base support having a substantially nonabsorbent surface, and a coating existing essentially of a composition of lip cosmetic. The composition has an amorphous, noncrystalline structure, and the coating is of a thickness of between 0.5 mils and 5 mils. The applicator permits the cosmetic to be applied with relative ease.

8 Claims, No Drawings

COSMETIC APPLICATOR

FIELD OF THE INVENTION

This invention relates to a cosmetic applicator for applying a cosmetic composition, particularly lipstick, to an epidermal surface in a measured amount and in a single application.

BACKGROUND OF THE INVENTION

The cosmetic industry has long sought a low-cost application device which can apply a premeasured amount of cosmetic, particularly lipstick, to an epidermal surface in a single application. Such an application device should permit the cosmetic to be easily applied, and, preferably, by a simple, single placement or impression. Apart from conventional tubes and their pencil-shaped derivatives, individual lipstick application devices are currently used chiefly to sample lipstick and require an indirect means for placement of the lip cosmetic on the lips. Independent of the application, the lip cosmetic should have the same characteristics and the same texture and feel after application as when applied using a conventional tube of lipstick of the same formulation. It is for this reason, individual lipstick application devices are, at present, limited commercially and, in general, to the use of miniaturized tubes or brush application devices, notwithstanding a plethora of current literature covering a multitude of different types of applicators for applying lip cosmetic.

Not only must the lip cosmetic be easily applied to the lips, ideally it should also be long-lasting. Currently, lipsticks are classified as being relatively easy to apply, i.e., possess a creamy consistency, or are relatively hard to apply. The relatively easy to apply lipsticks tend to come off the lips very easily when drinking, eating, or smoking, while the harder to apply lipsticks are more durable and tend to be long-lasting. Accordingly, to the lipstick user, a trade-off is required between the desirability of using an easy-to-apply lipstick having a creamy consistency, and using the more durable long-lasting lipsticks which are difficult to apply. At present, this choice is common to all lipsticks, independent of formulation.

It should be understood that a cosmetic lipstick formulation is a complex composition having a solid, waxy base containing dissolved and suspended colorants, as well as preservatives, fragrances, or flavors. All lipsticks are sold commercially in crystalline form. During crystallization, the oils are entrapped in a honeycomb-like formation, common to the micelle structure formed by the wax component. The composition of the lip formulation may be modified to adjust its consistency and its ease of application, primarily by the selection of the wax component and its concentration. The harder, "longer-wearing lipsticks" contain harder waxes and less oils, which make them difficult to apply.

SUMMARY OF THE INVENTION

A cosmetic applicator has been discovered, in accordance with the present invention, which permits a premeasured amount of any lip cosmetic formulation to be applied, preferably in a single application, with relative ease, while possessing a wear characteristic at least equal to the wear characteristic when applied from a conventional tube applicator.

The cosmetic applicator of the present invention broadly comprises a base support having a nonabsorbent surface, and a coating consisting essentially of a lip cosmetic composition, with the coating having an amorphous, noncrystalline form and a thickness in a range of between 0.5 mils and 5 mils.

DETAILED DESCRIPTION OF A PREFERRED EMBODIMENT OF THE INVENTION

The properties of lipstick considered by users to be the most desirable include the following: color, ease of application, smoothness, texture, i.e., how it feels on the lips, color-lasting, non-smearing, moisturizing, and softening attributes. A good lipstick will satisfy all or most of the above requirements. The attainment of these properties has become as much an art as a science. Some of the above properties, such as ease of application, smoothness, color-lasting, and texture, are, to some extent, physical attributes, which are enhanced using the applicator of the present invention, for any given lip cosmetic composition. The applicator is constructed from a base support having a coating of lip cosmetic in an amorphous, noncrystalline form, having a thickness of between 0.5 mils and 5 mils.

Lipstick is conventionally transferred to the lips by an applicator consisting of a tube containing a stick of lipstick, or by using a brush. A lip cosmetic may also be readily transferred to the lips in a convenient manner from an applicator consisting of a piece of paper folded over on itself to form two flaps, as described in U.S. Pat. No. 4,661,661, the description of which is herein incorporated by reference. The folded-over piece of paper contains a layer of lip cosmetic on each flap. The two flaps are reverse folded so that the lip cosmetic is exposed on each of the flaps. The applicator is then inserted between the lips so that the lips may be compressed over the lip cosmetic, while the applicator is pulled out from the lips, leaving a transferred deposit of lipstick on the lips.

The aforementioned patent specification teaches coating the lip cosmetic on the piece of paper using any conventional coating technique, and specifically identifies known printing equipment, such as a flatbed press, a rotary press, a web press, etc., or by means of silk-screening. It is not, however, apparent from the aforementioned patent how to actually apply lip cosmetic to the paper surface with sufficient thickness to enable the lip cosmetic to be transferred to the lips, with enough lip cosmetic deposited on the lips to satisfy a typical user, much less how to achieve the desired properties of ease of application, texture, and color-lasting. Instead, the aforementioned patent addresses how to construct a low-cost, sanitary applicator for an application of lip cosmetic to the lips from a piece of paper.

The amorphous structure of the lip cosmetic within a given thickness range controls the ease of application of lip cosmetic on the lips. Contrary to conventional thinking, a lip cosmetic coating in an amorphous noncrystalline form between 0.5 mils to 5 mils thick is easier to apply to the lips and has the same or better wear characteristics than its counterpart of identical composition with a crystalline structure. It is hypothesized that this is because mechanical energy is required to break down the crystalline structure when using a conventional tube of lipstick or a brush. In fact, a conventional "hard" lip cosmetic formulation with a long-lasting characteristic can be applied, using the applicator of the present invention, with much greater ease of application, while retaining the long-lasting wear characteristic of the lipstick. To achieve this result, the lipstick formulation is converted to an amorphous, noncrystalline form or is preserved in an amorphous, noncrystalline form during manufacture, and is then coated onto a transfer surface of any composition which has a substantially nonabsorbent characteristic, in a thickness range of between 0.5 mils to 5 mils. The lower end of the thickness range is a practical limitation, below which insufficient lip cosmetic is present to satisfy a typical user. Conversely, if the coating is too thick, i.e., above 5 mils, the applicator is no longer a control medium for transferring lip cosmetic to the lips. The preferred coating thickness is between 1 mil and 3 mils.

To maintain or preserve the amorphous structure, the lip cosmetic formulation cannot be heated above its melting temperature, and then allowed to cool and solidify. This will inherently cause the lip cosmetic composition to crystallize. Accordingly, any method may be used to form a lip cosmetic coating on a base surface having the desired thickness, provided the lip cosmetic formulation is not liquid at the outset and is not heated above its melting temperature. Any conventional lipstick formulated composition may be used. If the composition is crystalline, it must first be converted to a noncrystalline, amorphous state. This is preferably accomplished by the application of mechanical energy using, for example, blending and/or stirring equipment at controlled mixing speeds, to avoid heating the composition above its melting temperature. The lip cosmetic should be mixed relatively slowly to maintain the lipstick in a highly viscous state until a uniform, homogeneous consistency is reached, without melting the lip cosmetic. Any commercially available mixer may be used for this purpose. The mixing operation modifies the crystalline structure into an amorphous structure.

The amorphous lip cosmetic is then applied to the base support without melting it. The amorphous lip cosmetic may be applied by hand-coating, brushing, or painting, or by using any commercially available coating device. It is preferable to apply the amorphous lip cosmetic in an unadulterated state. A preferred coating method is screen printing, with the screen printing operation conducted by hand or by using a manual- or power-operated commercial press having either a flat screen or a cylindrical screen. The screen may be made of silk, plastic, or metallic mesh. The screen may have an open mesh, with a mesh count of preferably between 80 to 420 per lineal inch.

In a simple screen printing operation, a squeegee is moved in a sweeping motion over a flat screen against a head of viscous, amorphous lip cosmetic which is applied over the screen in advance of the squeegee. A cylindrical rotary screen, perforated metal, or a stencil may also be used. The thickness of The coating is readily controlled in one pass.

The base support on which the lip cosmetic is coated may have a flat surface. If the applicator is not to be used immediately, it is preferable that the applicator be protected using an irregular surface geometry formed by raised projections, as is taught and disclosed in U.S. Pat. No. 4,995,408, the disclosure of which is herein incorporated by reference. The raised projections may be of any particular shape or geometry, and may form any pattern or arrangement over the base support. In general, the number of projections should occupy at least about three percent (3%), and preferably five percent (5%) minimum, of the surface area of the base support on which the lipstick is coated. The projections may be formed by any molding, coining, laminating, or embossing operation. The raised projections maintain a separation between the cover and the amorphous lipstick and, more importantly, protect the coating applicator during packaging and handling, as explained in the aforementioned patent. The projections should extend through the lipstick coating, i.e., should be longer in length than the coating thickness. The base material on which the lipstick is coated is not, of itself, important, and may be of any composition, but should preferably be nonabsorbent or coated with a nonabsorbent coating, e.g., polyethylene or other suitable plastic materials for forming a laminated structure.

What is claimed is:

1. A cosmetic applicator comprising a base support having a substantially nonabsorbent surface, and a coating consisting essentially of a cosmetic composition of lip cosmetic having a thickness of between 0.5 mils and 5 mils which is of uniform homogeneous consistency and has an amorphous noncrystalline structure throughout its thickness.

2. A cosmetic applicator, as defined in claim 1, wherein the coating thickness is between 1 mil and 3 mils.

3. A cosmetic applicator, as defined in claim 2, wherein said base support has an irregular surface over which said cosmetic composition is coated.

4. A cosmetic applicator, as defined in claim 3, wherein said irregular surface geometry is formed by a multiplicity of raised projections which extend through the coating.

5. A cosmetic applicator, as defined in claim 4, wherein said raised projections should occupy at least three percent (3%) of the surface area of the base support.

6. A cosmetic applicator, as defined in claim 1, wherein said coating is screen printed in its amorphous form.

7. A cosmetic applicator for transferring lip cosmetic to human lips comprising a base support having a substantially nonabsorbent surface, and a coating consisting essentially of a lip cosmetic composition of uniform homogeneous consistency with a thickness of between 0.5 mils and 5 mils and an amorphous noncrystalline structure throughout its thickness formed by mechanically blending said cosmetic composition at a temperature below the melting temperature of said lip cosmetic composition to form said uniform homogeneous consistency and amorphous structure throughout the thickness of said lip cosmetic and screen printing the blended mass upon said base without the application of heat.

8. A cosmetic applicator as defined in claim 7 wherein the lip cosmetic is screen printed through a screen having a mesh count of between 80 and 420 per lineal inch.

* * * * *